(12) United States Patent
Dahanukar et al.

(10) Patent No.: US 7,786,301 B2
(45) Date of Patent: *Aug. 31, 2010

(54) PROCESS FOR PREPARING XANTHINE PHOSPHODIESTERASE V INHIBITORS AND PRECURSORS THEREOF

(75) Inventors: Vilas A. Dahanukar, Edison, NJ (US); Hoa N. Nguyen, Dayton, NJ (US); Cecilia A. Orr, Clark, NJ (US); Fucheng Zhang, Edison, NJ (US); Ilia Zavialov, Princeton, NJ (US)

(73) Assignee: Schering Corporation, Kenilworth, NJ (US)

( * ) Notice: Subject to any disclaimer, the term of this patent is extended or adjusted under 35 U.S.C. 154(b) by 1044 days.

This patent is subject to a terminal disclaimer.

(21) Appl. No.: 11/429,719

(22) Filed: May 8, 2006

(65) Prior Publication Data

US 2006/0205943 A1    Sep. 14, 2006

Related U.S. Application Data

(63) Continuation of application No. 10/449,526, filed on May 30, 2003, now Pat. No. 7,074,923.

(60) Provisional application No. 60/384,478, filed on May 31, 2002.

(51) Int. Cl.
  C07D 473/06    (2006.01)
  C07D 473/08    (2006.01)
  C07D 233/90    (2006.01)

(52) U.S. Cl. .................................................. 544/272
(58) Field of Classification Search ................ 544/267, 544/271, 272, 273
See application file for complete search history.

(56) References Cited

U.S. PATENT DOCUMENTS

| | | | | |
|---|---|---|---|---|
| 5,319,080 | A * | 6/1994 | Leumann | 536/27.1 |
| 5,393,755 | A * | 2/1995 | Neustadt et al. | 514/233.2 |
| 6,214,992 | B1 * | 4/2001 | Gebert et al. | 544/267 |
| 6,821,978 | B2 * | 11/2004 | Chackalamannil et al. | 514/262.1 |
| 7,235,538 | B2 * | 6/2007 | Kanstrup et al. | 514/81 |
| 2002/0161001 | A1 * | 10/2002 | Kanstrup et al. | 514/218 |
| 2002/0198205 | A1 * | 12/2002 | Himmelsbach et al. | 514/234.5 |
| 2003/0087918 | A1 * | 5/2003 | Belleau et al. | 514/263.23 |
| 2003/0105077 | A1 * | 6/2003 | Kanstrup et al. | 514/217.06 |
| 2003/0199528 | A1 * | 10/2003 | Kanstrup et al. | 514/263.2 |
| 2003/0232845 | A1 * | 12/2003 | Dahanukar et al. | 514/263.36 |
| 2003/0236272 | A1 * | 12/2003 | Carr | 514/263.2 |
| 2004/0077645 | A1 * | 4/2004 | Himmelsbach et al. | 514/234.5 |
| 2004/0087587 | A1 * | 5/2004 | Himmelsbach et al. | 514/234.5 |
| 2007/0027168 | A1 * | 2/2007 | Pfrengle et al. | 514/263.22 |

FOREIGN PATENT DOCUMENTS

JP    05001065 A  *  1/1993

| | | | |
|---|---|---|---|
| WO | WO 0224698 | A1 * | 3/2002 |
| WO | WO 2004009091 | A1 * | 1/2004 |
| WO | WO 2004018468 | A2 * | 3/2004 |
| WO | WO 2004033455 | A2 * | 4/2004 |
| WO | WO 2004048379 | A1 * | 6/2004 |

OTHER PUBLICATIONS

Chlon, Grazyna et al., Polish Journal of Pharmacology (2001), 53(4), 359-368.*

* cited by examiner

*Primary Examiner*—Mark L Berch
(74) *Attorney, Agent, or Firm*—Patent Practitioners of Schering Corporation; H. Eric Fischer

(57) ABSTRACT

A process for preparing xanthine phosphodiesterase V inhibitors, and compounds utilized in said process. The process includes a five-step methodology for efficient synthesis of Compound 5 without intermediate purifications or separations, a dihalogenation step to synthesize Compound 7, and a coupling reaction to produce Compound 9.

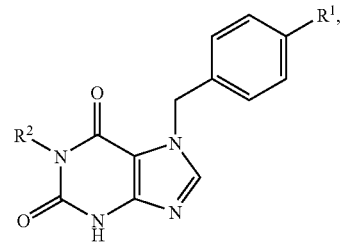

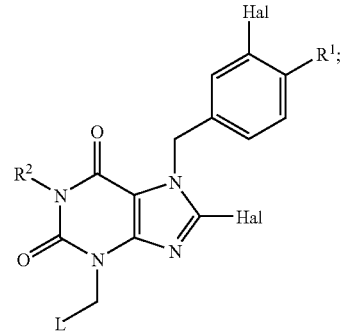

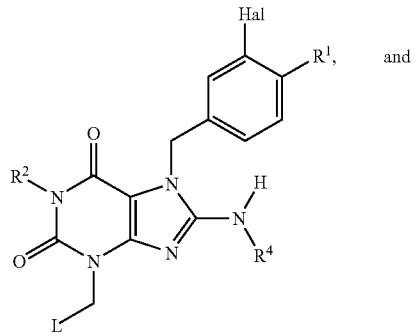

and

3 Claims, No Drawings

PROCESS FOR PREPARING XANTHINE PHOSPHODIESTERASE V INHIBITORS AND PRECURSORS THEREOF

CROSS-REFERENCE TO RELATED PATENT APPLICATION

This is a Continuation of U.S. patent application Ser. No. 10/449,526, filed May 30, 2004, which application is incorporated herein in its entirety by reference, and which application in turn claims priority under 35 USC section 119(e) to U.S. Provisional Application Ser. No. 60/384,478, filed May 31, 2002, which application is also incorporated by reference herein as if fully set forth.

FIELD OF THE INVENTION

The invention relates to a process for preparing polycyclic xanthine phosphodiesterase V ("PDE V") inhibitors. The invention further relates to compounds useful for preparing PDE V inhibitors.

BACKGROUND

Processes for preparing PDE V inhibitor compounds can be found in U.S. Pat. No. 6,207,829, U.S. Pat. No. 6,066,735, U.S. Pat. No. 5,955,611, U.S. Pat. No. 5,939,419, U.S. Pat. No. 5,393,755, U.S. Pat. No. 5,409,934, U.S. Pat. No. 5,470,579, U.S. Pat. No. 5,250,534, WO 02/24698, WO 99/24433, WO 93/23401, WO 92/05176, WO 92/05175, EP 740,668 and EP 702,555. One type of PDE V inhibitor compound contains a xanthine functionality in its structure. Xanthines can be prepared as described by Peter K. Bridson and Xiaodong Wang in 1-*Substituted Xanthines, Synthesis*, 855 (July, 1995), which is incorporated herein by reference in its entirety. WO 02/24698, which is incorporated herein by reference in its entirety, teaches a class of xanthine PDE V inhibitor compounds useful for the treatment of impotence. A general process disclosed therein for preparing xanthine PDE V inhibitor compounds having the formula (I) follows:

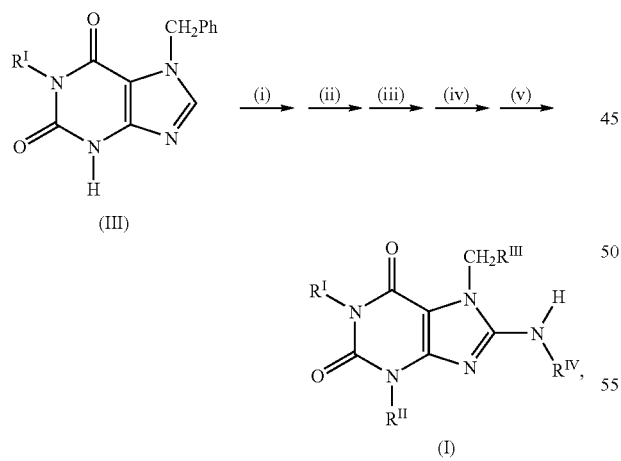

(i) reacting a compound having the formula (III) with an alkyl halide in the presence of a base (introduction of $R^{II}$ or a protected form of $R^{II}$);
(ii) (a) debenzylating and then (b) alkylating the compound resulting from step (i) with an alkyl halide, $XCH_2R^{III}$;
(iii) (a) deprotonating and then (b) halogenating the compound resulting from step (ii);
(iv) reacting the compound resulting from step (iii) with an amine having the formula $R^{IV}NH_2$; and
(v) removing a protecting portion of $R^{II}$, if present, on the compound resulting from step (iv) to form the compound having the formula (I).

$R^I$, $R^{II}$, $R^{III}$ and $R^{IV}$ correspond to $R^1$, $R^2$, $R^3$ and $R^4$, respectively, in WO 02/24698, and are defined therein. WO 02/24698 (pages 44 and 68-73) also teaches a synthesis for the following xanthine compound (identified therein as Compound 13 or Compound 114 of Table II): 1-ethyl-3,7-dihydro-8-[(1R,2R)-(hydroxycyclopentyl)amino]-3-(2-hydroxyethyl)-7-[(3-bromo-4-methoxyphenyl)methyl]-1H-purine-2,6-dione:

Compound 13

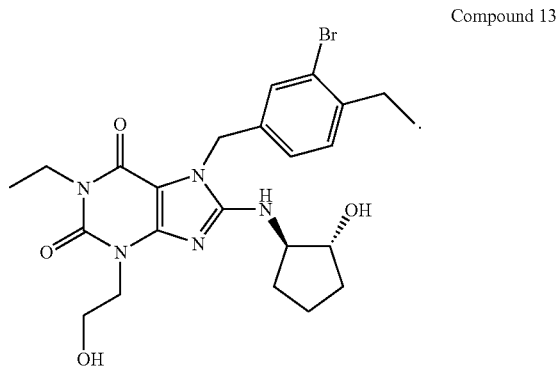

It would be beneficial to provide an improved process for preparing polycyclic xanthine PDE V inhibitor compounds. It would further be beneficial if the process provided high yields without the need for chromatographic purification. It would still further be beneficial if the process provided compounds of high thermodynamic stability. It would be still further beneficial to provide intermediate compounds that can be used in the improved process. The invention seeks to provide these and other benefits, which will become apparent as the description progresses.

SUMMARY OF THE INVENTION

One aspect of the invention is a method for preparing a Compound 13, comprising:
(a) reacting glycine ethyl ester or a salt thereof with

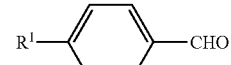

to form

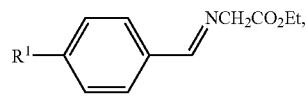

wherein Et is $CH_3CH_2$—,
(b) reducing

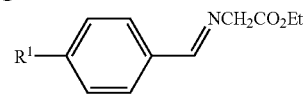

to form a Compound 1:

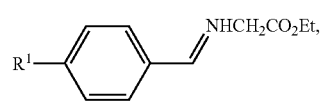

(c) reacting cyanamide with an excess of triethylorthoformate to form a Compound 2:

$$NC-N=\overset{H}{\underset{}{C}}-OEt,\qquad 2$$

(d) reacting the Compound 2 with the Compound 1 to form a Compound 3:

3

[Structure of Compound 3: benzyl group with R¹ para-substituent, attached to N bearing EtO₂C-CH₂ group and =CH-NH linkage to cyanamide N=C=N]

(e) reacting the Compound 3 with a base to form a Compound 4:

4

[Structure of Compound 4: imidazole with EtO(O)C- at one position, H₂N- at adjacent position, and N-benzyl with R¹ para-substituent]

(f) reacting the Compound 4 with R²NHCO₂R¹ in the presence of a metallic base to form a Compound Salt 5K:

5K

[Structure of Compound Salt 5K: xanthine core with R² on N1, N7-benzyl (R¹ para), and M⁺ counterion at N3⁻]

wherein M⁺ is a metal ion, (g) optionally, reacting the Compound Salt 5K with an acid to form a Compound 5:

5

[Structure of Compound 5: xanthine with R² on N1, N7-benzyl-R¹, NH at N3]

(h) reacting the Compound Salt 5K or the Compound 5 with BrCH₂L in the presence of a phase transfer catalyst to form a Compound 6:

6

[Structure of Compound 6: xanthine with R² on N1, N7-benzyl-R¹, N3-CH₂L]

wherein L is R³ or a protected form of R³ comprising R³ with a protective substituent selected from the group consisting of acetate, propionate, pivaloyl, —OC(O)R⁵, —NC(O)R⁵ and —SC(O)R⁵ group, wherein R⁵ is H or $C_{1-12}$ alkyl;

(i) dihalogenating the Compound 6 to form a Compound 7:

7

[Structure of Compound 7: like Compound 6 with Hal on benzyl ring and Hal at C8]

(j) reacting the Compound 7 with R⁴NH₂, and adding a base thereto, to form a Compound 9:

9

[Structure of Compound 9: xanthine with Hal on benzyl, C8-NHR⁴, N3-CH₂L]

and (k) (i) when L is R³, the Compound 9 is a Compound 13, and
(ii) when L is a protected form of R³, reacting the Compound 9 with a base to form the Compound 13:

13

[Structure of Compound 13: xanthine with Hal on benzyl, C8-NHR⁴, N3-CH₂R³]

wherein, $R^1$, $R^2$ and $R^3$ are each independently selected from the group consisting of:

H, alkyl, alkenyl, alkynyl, cycloalkyl, aryl, heteroaryl, allyl, —$OR^5$,
—C(O)$OR^5$, —C(O)$R^5$, —C(O)N($R^5$)$_2$, —NHC(O)$R^5$ and —NHC(O)$OR^5$, wherein each $R^5$ is independently H or alkyl;

provided that $R^2$ and $R^3$ are not both —H;

$R^4$ is an alkyl, cycloalkyl, cycloalkenyl, heterocycloalkyl, aryl or heteroaryl group;

wherein $R^1$, $R^2$, $R^3$ and $R^4$ are optionally substituted with one or more moieties independently selected from the group consisting of: alkyl, cycloalkyl, alkenyl, cycloalkenyl, alkynyl, aryl, heteroaryl, heterocycloalkyl, halo, thio, nitro, oximino, acetate, propionate, pivaloyl, —OC(O)$R^5$, —NC(O)$R^5$ or —SC(O)$R^5$, —$OR^{50}$, —N$R^{50}R^{51}$, —C(O)$OR^{50}$, —C(O)$R^{50}$, —SO$_{0-2}R^{50}$, —SO$_2$N$R^{50}R^{51}$, —N$R^{52}$SO$_2R^{50}$, =C($R^{50}R^{51}$), =NO$R^{50}$, =NCN, =C(halo)$_2$, =S, =O, —C(O)N($R^{50}R^{51}$), —OC(O)$R^{50}$, —OC(O)N($R^{50}R^{51}$), —N($R^{52}$)C(O)($R^{50}$), —N($R^{52}$)C(O)$OR^{50}$ and —N($R^{52}$)C(O)N($R^{50}R^{51}$), wherein each $R^5$ is independently H or alkyl and $R^{50}$, $R^{51}$ and $R^{52}$ are each independently selected from the group consisting of: H, alkyl, cycloalkyl, heterocycloalkyl, heteroaryl and aryl, and when chemically feasible, $R^{50}$ and $R^{51}$ can be joined together to form a carbocyclic or heterocyclic ring;

Et is CH$_3$CH$_2$—;

Hal is a halogen group; and

L is a protected form of $R^3$ comprising $R^3$ with a protective substituent selected from the group consisting of acetate, propionate, pivaloyl, —OC(O)$R^5$, —NC(O)$R^5$ and —SC(O)$R^5$ group, wherein $R^5$ is H or $C_{1-12}$ alkyl.

A further understanding of the invention will be had from the following detailed description of the invention.

DETAILED DESCRIPTION

Definitions and Usage of Terms

The following definitions and terms are used herein or are otherwise known to a skilled artisan. Except where stated otherwise, the definitions apply throughout the specification and claims. Chemical names, common names and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (two or more terms that are combined to identify a single moiety) to a subject structure is through the last named term of the multiple term substituent. For example, a cycloalkylalkyl substituent attaches to a targeted structure through the latter "alkyl" portion of the substituent (e.g., structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)— or —C(=O)—. Similarly, a double bond between a sulfur atom and an oxygen atom may be represented in a chemical formula by —SO—, —S(O)— or —S(=O)—. One skilled in the art will be able to determine the presence or absence of double (and triple bonds) in a covalently-bonded molecule. For instance, it is readily recognized that a carboxyl functionality may be represented by —COOH, —C(O)OH, —C(=O)OH or —CO$_2$H.

The term "substituted," as used herein, means the replacement of one or more atoms or radicals, usually hydrogen atoms, in a given structure with an atom or radical selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, heterocycloalkyl, aryl and heteroaryl groups, independently of or together with one another, may be substituents on any of the specified groups, unless otherwise indicated.

The term "optionally substituted" means, alternatively, not substituted or substituted with the specified groups, radicals or moieties. It should be noted that any atom with unsatisfied valences in the text, schemes, examples and tables herein is assumed to have the hydrogen atom(s) to satisfy the valences.

The term "chemically-feasible" is usually applied to a ring structure present in a compound and means that the ring structure (e.g., the 4- to 7-membered ring, optionally substituted by . . . ) would be expected to be stable by a skilled artisan.

The term "heteroatom," as used herein, means a nitrogen, sulfur or oxygen atom. Multiple heteroatoms in the same group may be the same or different.

As used herein, the term "alkyl" means an aliphatic hydrocarbon group that can be straight or branched and comprises 1 to about 24 carbon atoms in the chain. Preferred alkyl groups comprise 1 to about 15 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. The alkyl can be substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. The alkenyl group can be substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Alkoxy" means an alkyl-O-group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

The term "cycloalkyl" as used herein, means an unsubstituted or substituted, saturated, stable, non-aromatic, chemically-feasible carbocyclic ring having preferably from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, or the like.

The term "hydrocarbon," as used herein, means a compound, radical or chain consisting of only carbon and hydrogen atoms, including aliphatic, aromatic, normal, saturated and unsaturated hydrocarbons.

The term "alkenyl," as used herein, means an unsubstituted or substituted, straight or branched, hydrocarbon chain having at least one double bond present and, preferably, from two to fifteen carbon atoms, more preferably, from two to twelve carbon atoms.

The term "cycloalkenyl," as used herein, means an unsubstituted or substituted, unsaturated carbocyclic ring having at least one double bond present and, preferably, from three to fifteen carbon atoms, more preferably, from five to eight carbon atoms. A cycloalkenyl goup is an unsaturated carbocyclic group. Examples of cycloalkenyl groups include cyclopentenyl and cyclohexenyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 10 carbon atoms in the chain; and more preferably about 2 to about 6 carbon atoms in the chain. Branched means that one or more lower alkyl groups such as methyl, ethyl or propyl, are attached to a linear alkynyl chain. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, aryl and cycloalkyl.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl, or the like. If desired, the carbocyclic moiety can be substituted with from one to five, preferably, one to three, moieties, such as mono- through pentahalo, alkyl, trifluoromethyl, phenyl, hydroxy, alkoxy, phenoxy, amino, monoalkylamino, dialkylamino, or the like.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. Mono- and polycyclic (e.g., bicyclic) heteroaryl groups can be unsubstituted or substituted with a plurality of substituents, preferably, one to five substituents, more preferably, one, two or three substituents (e.g., mono- through pentahalo, alkyl, trifluoromethyl, phenyl, hydroxy, alkoxy, phenoxy, amino, monoalkylamino, dialkylamino, or the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocycloalkyl," as used herein, means an unsubstituted or substituted, saturated, chemically-feasible cyclic ring system having from three to fifteen members, preferably, from three to eight members, and comprising carbon atoms and at least one heteroatom as part of the ring.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, more preferably, five to seven atoms. Polycyclic ring systems consisting of two rings preferably contain from six to sixteen atoms, most preferably, ten to twelve atoms. Polycyclic ring systems consisting of three rings contain preferably from thirteen to seventeen atoms, more preferably, fourteen or fifteen atoms. Each heterocyclic ring has at least one heteroatom. Unless otherwise stated, the heteroatoms may each be independently selected from the group consisting of nitrogen, sulfur and oxygen atoms.

The term "carbocyclic ring" or "carbocycle," as used herein, means an unsubstituted or substituted, saturated, unsaturated or aromatic (e.g., aryl), chemically-feasible hydrocarbon ring, unless otherwise specifically identified. Carbocycles may be monocyclic or polycyclic. Monocyclic rings, preferably, contain from three to eight atoms, more preferably, five to seven atoms. Polycyclic rings having two rings, preferably, contain from six to sixteen atoms, more preferably, ten to twelve atoms, and those having three rings, preferably, contain from thirteen to seventeen atoms, more preferably, fourteen or fifteen atoms.

The term "hydroxyalkyl," as used herein, means a substituted hydrocarbon chain preferably an alkyl group, having at least one hydroxy substituent (-alkyl-OH). Additional substituents to the alkyl group may also be present. Representative hydroxyalkyl groups include hydroxymethyl, hydroxyethyl and hydroxypropyl groups.

The terms "Hal," "halo," "halogen" and "halide," as used herein, mean a chloro, bromo, fluoro or iodo atom radical. Chlorides, bromides and fluorides are preferred halides.

The term "thio," as used herein, means an organic acid radical in which divalent sulfur has replaced some or all of the oxygen atoms of the carboxyl group. Examples include —$R^{53}$C(O)SH, —$R^{53}$C(S)OH and —$R^{53}$C(S)SH, wherein $R^{53}$ is a hydrocarbon radical.

The term "nitro," as used herein, means the —N(O)$_2$ radical.

The term "allyl," as used herein, means the —C$_3$H$_5$ radical.

The term "phase transfer catalyst," as used herein, means a material that catalyzes a reaction between a moiety that is soluble in a first phase, e.g., an alcohol phase, and another moiety that is soluble in a second phase, e.g., an aqueous phase.

The following abbreviations are used in this application: EtOH is ethanol; Me is methyl; Et is ethyl; Bu is butyl; n-Bu is normal-butyl, t-Bu is tert-butyl, OAc is acetate; KOt-Bu is potassium tert-butoxide; NBS is N-bromo succinimide; NMP is 1-methyl-2-pyrrolidinone; DMA is N,N-dimethylacetamide; n-Bu$_4$NBr is tetrabutylammonium bromide; n-Bu$_4$NOH is tetrabutylammonium hydroxide, n-Bu$_4$NH$_2$SO$_4$ is tetrabutylammonium hydrogen sulfate, and equiv. is equivalents.

In certain of the chemical structures depicted herein, certain compounds are racemic, i.e., a mixture of dextro- and levorotatory optically active isomers in equal amounts, the resulting mixture having no rotary power.

General Synthesis

One aspect of the invention comprises a general synthesis of xanthines based on a one-pot, five-step sequence from cyanamide and N-aryl glycine ester. Compound 1 can be prepared from glycine ethyl ester or a salt thereof (e.g., hydrochloric or sulfuric acid salt) and an aromatic aldehyde. As shown in Scheme I below, Compound 1 is prepared from glycine ethyl ester hydrochloride and an aromatic aldehyde. Compound 2 is prepared by reacting cyanamide with an excess of triethylorthoformate. Compound 3 is prepared by reacting Compound 2 with Compound 1. Compound 3 is converted into Compound 4 by reacting it with a base (e.g., potassium tert-butoxide). Compound 4 is reacted with a N—R$^2$-substituted carbamate (e.g., urethane) in the presence of a base to obtain Compound Salt 5K. Based on the N—R$^2$-substituent of the carbamate used, a desired N-1-R$^2$-substituted xanthine Compound Salt 5K is obtained. Compound Salt 5K is then N-3-L-substituted with an L-halide using a phase transfer catalyst to provide a tri-substituted (R$^1$, R$^2$ and L) xanthine Compound 6. Alternatively, Compound Salt 5K can be neutralized to Compound 5, which can then be selectively N-L-substituted to provide Compound 6. A selective dihalogenation of Compound 6 leads to a dihalo Compound 7, which is then coupled with an R$^4$-substituted amine, followed by an addition of a base (e.g., sodium bicarbonate), to provide a tetrasubstituted (R$^1$, R$^2$, R$^3$ and R$^4$) xanthine Compound 13 when L is the same as R$^3$. If L is a protected form of R$^3$, intermediate Compound 9 is deprotected with a base (e.g., tetrabutylammonium hydroxide) to provide the tetrasubstituted (R$^1$, R$^2$, R$^3$ and R$^4$) xanthine Compound 13. Scheme I depicts this process:

Scheme I: General Synthesis of Xanthines

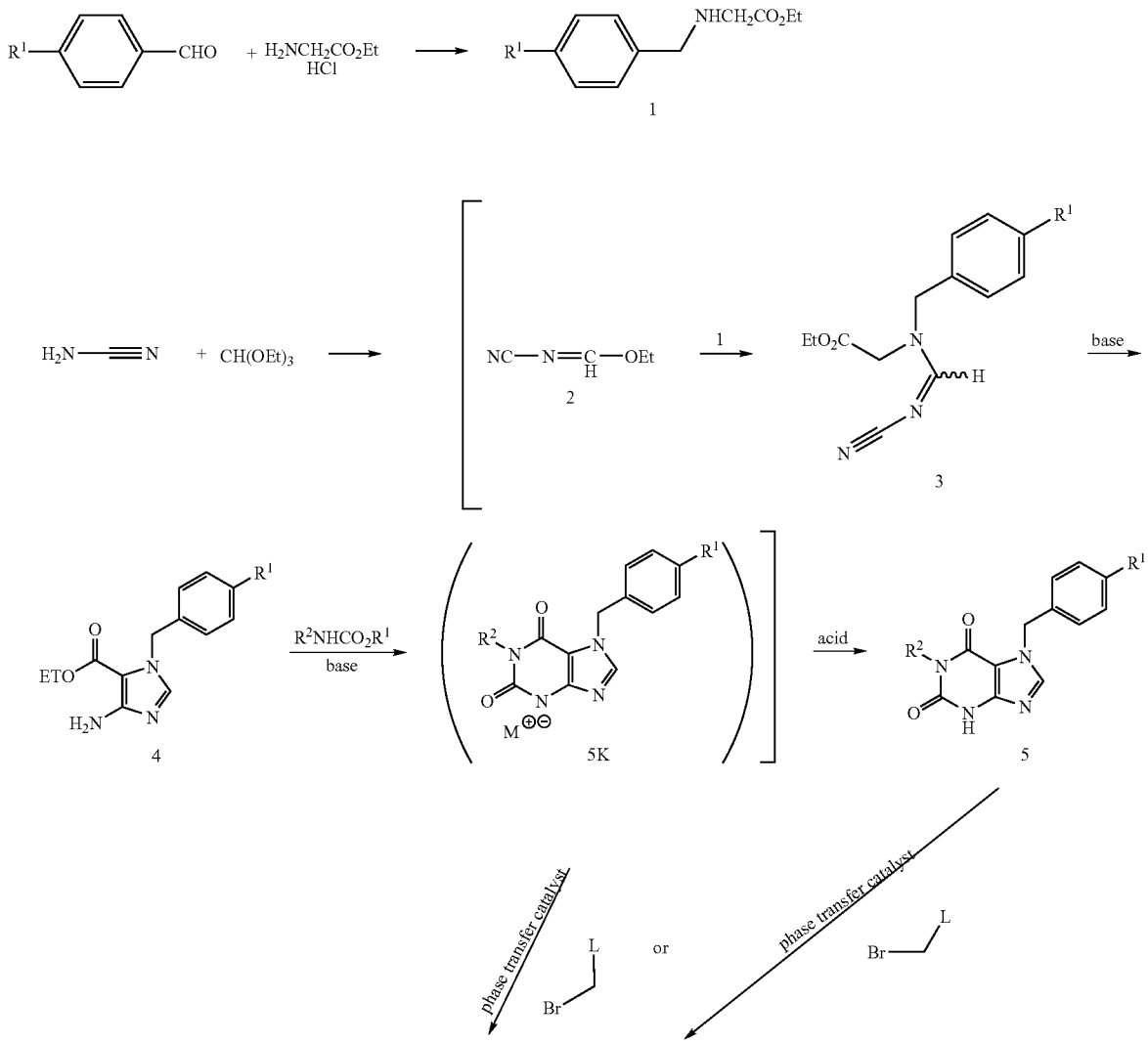

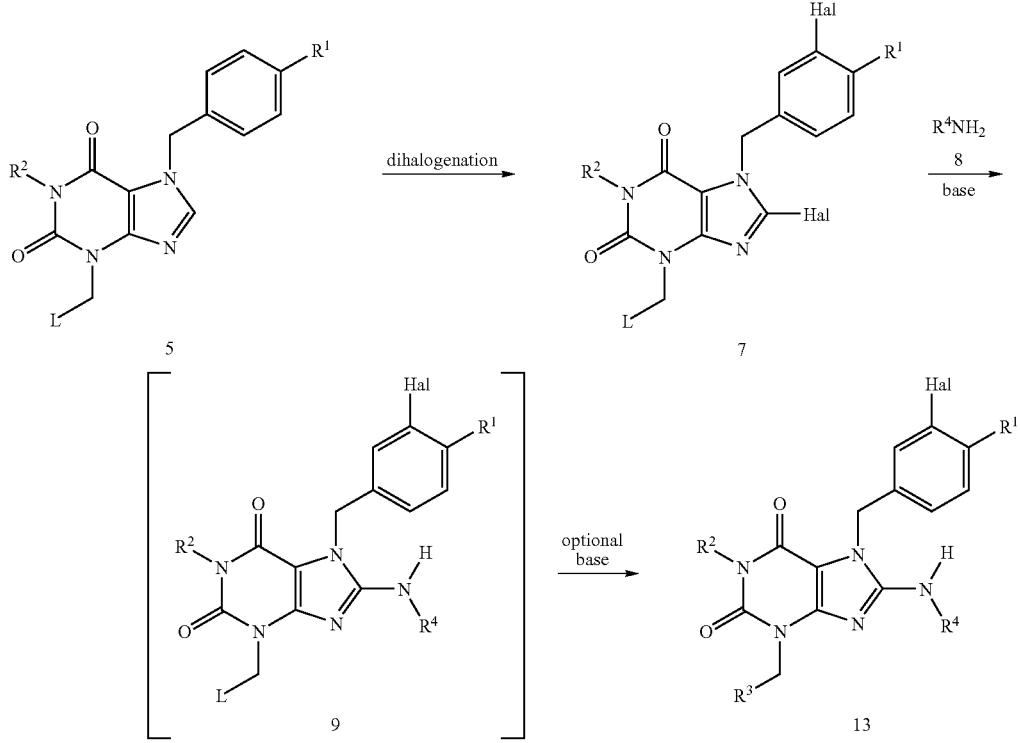

wherein,

R¹, R² and R³ are each independently selected from the group consisting of:

H, alkyl, alkenyl, alkynyl, cycloalkyl, aryl, heteroaryl, allyl, —OR⁵,
—C(O)OR⁵, —C(O)R⁵, —C(O)N(R⁵)₂, —NHC(O)R⁵ and —NHC(O)OR⁵, wherein each R⁵ is independently H or alkyl;

provided that R² and R³ are not both —H;

R⁴ is an alkyl, cycloalkyl, cycloalkenyl, heterocycloalkyl, aryl or heteroaryl group;

wherein R¹, R², R³ and R⁴ are optionally substituted with moieties independently selected from the group consisting of: alkyl, cycloalkyl, alkenyl, cycloalkenyl, alkynyl, aryl, heteroaryl, heterocycloalkyl, halo, thio, nitro, oximino, acetate, propionate, pivaloyl, —OC(O)R⁵, —NC(O)R⁵ or —SC(O)R⁵, —OR⁵⁰, —NR⁵⁰R⁵¹, —C(O)OR⁵⁰, —C(O)R⁵⁰, —SO₀₋₂R⁵⁰, —SO₂NR⁵OR⁵¹, —NR⁵²SO₂R⁵⁰, =C(R⁵⁰R⁵¹), =NOR⁵⁰, =NCN, =C(halo)₂, =S, =O, —C(O)N(R⁵⁰R⁵¹), —OC(O)R⁵⁰, —OC(O)N(R⁵⁰R⁵¹), —N(R⁵²)C(O)(R⁵⁰), —N(R⁵²)C(O)OR⁵⁰ and —N(R⁵²)C(O)N(R⁵⁰R⁵¹), wherein each R⁵ is independently H or alkyl and R⁵⁰, R⁵¹ and R⁵² are each independently selected from the group consisting of: H, alkyl, cycloalkyl, heterocycloalkyl, heteroaryl and aryl;

Hal is a halogen group;

L is R³ or a protected form of R³ comprising R³ with a protective substituent selected from the group consisting of acetate, propionate, pivaloyl, —OC(O)R⁵, —NC(O)R⁵ and —SC(O)R⁵ group, wherein R⁵ is H or alkyl; and M⁺ is a metal ion.

While some compounds are shown in Scheme I as non-isolated intermediates, it is understood that they can be isolated using routine chemistry techniques.

Preferred embodiments of the invention utilize compounds with the following R¹, R², R³ and R⁴ radicals:

R¹ is preferably alkyl, aryl, heteroaryl, —OR⁵, —C(O)OR⁵, —C(O)R⁵ or —C(O)N(R⁵)₂, wherein R⁵ is H or alkyl. Each R¹ group is optionally substituted as defined above. More preferably, R¹ is —OR⁵, wherein R⁵ is H or alkyl. Even more preferably, R¹ is alkoxy, such as methoxy.

R² is preferably $C_{1-12}$ alkyl, $C_{3-8}$ cycloalkyl, aryl or heteroaryl. Each R² group is optionally substituted as defined above. More preferably, R² is $C_{1-6}$ alkyl, optionally substituted as defined above. Even more preferably, R² is ethyl.

R³ is preferably $C_{1-12}$ alkyl, $C_{3-8}$ cycloalkyl, aryl, heteroaryl, allyl, —NHC(O)R⁵ or —NHC(O)OR⁵, wherein R⁵ is H or $C_{1-12}$ alkyl. Each R³ group is optionally substituted as defined above. More preferably, R³ is $C_{1-6}$ alkyl, optionally substituted with one of the groups defined above. Even more preferably, R³ is $C_{1-6}$ alkyl, substituted with —OR⁵⁰, wherein R⁵⁰ is H, such as hydroxymethyl.

R⁴ is preferably $C_{1-12}$ alkyl, $C_{3-8}$ cycloalkyl, $C_{5-8}$ cycloalkenyl, heterocycloalkyl, aryl or heteroaryl. Each R⁴ group is optionally substituted as defined above. More preferably, R⁴ is $C_{3-8}$ cycloalkyl, optionally substituted as defined above. Even more preferably, R⁴ is $C_{4-7}$ cycloalkyl, substituted with —OR⁵⁰, wherein R⁵⁰ is defined as above. For example, R⁴ can be 2-hydroxy cyclopentyl.

In some embodiments of the invention, L is the same as R³. In other embodiments of the invention, L is a protected form of R³, in which case the protective substituent on R³ is preferably an acetate, propionate, pivaloyl, —OC(O)R⁵, —NC(O)R⁵ or —SC(O)R⁵ group, wherein R⁵ is H or $C_{1-12}$ alkyl.

Hal is preferably chlorine, bromine and fluorine. More preferably, Hal is chlorine or bromine. Even more preferably, Hal is bromine.

M+ is, preferably, an alkali metal or alkaline earth metal ion. More preferably, M+ is a potassium or sodium ion.

Compound 1 can be prepared by reacting about equimolar amounts of p-anisaldehyde and glycine ethyl ester hydrochloride (or its free form) in the presence of a base (e.g., potassium carbonate, sodium carbonate, sodium bicarbonate, potassium butoxide, or the like) and in an alcoholic solvent (e.g., ethanol, isopropanol, or the like). Preferably, up to about 2 moles (e.g., about 1.3-1.5 moles) of glycine ethyl ester hydrochloride and up to about 2 moles (e.g., about 1 mole) of inorganic salt can each be used per mole of p-anisaldehyde. The reaction proceeds through an intermediate imine (not shown), which is reduced with a reducing agent (e.g., $NaBH_4$, catalytic hydrogenation, $H_2/Pd/C$, or the like), preferably, a borohydride reducing agent. The reaction can be run at room temperature. Preferably, the reaction is run at about 20-45° C., more preferably, about 30-40° C. At the end of the reaction, Compound 1 is isolated in a solution form in an organic solvent (e.g., toluene), and used as such for the next step.

Compound 2 is N-cyanomethanimidic acid ethyl ester, and is prepared by reacting cyanamide with an excess of triethylorthoformate. Preferably, from about 1.2 to about 1.5 moles of triethylorthoformate (e.g., 1.33 moles) are reacted with about 1 mole of cyanamide. Preferably, the reaction mixture is gradually heated up to about 85-95° C. for about 2 hours. Compound 2 is not isolated, and is used in-situ for the next step.

The structure of Compound 3 is novel. An equimolar reaction mixture of Compound 2 (obtained in-situ above) is added to a solution of Compound 1 in an anhydrous, ethereal organic solvent (e.g., tetrahydrofuran ("THF"), diethyl ether, monoethyl ether, monoglyme, diglyme, ethylene glycol, or the like), and heated to about 65-70° C. for about 1 hour. About 1.1 to about 1.3 moles (e.g., 1.2 moles) of Compound 2 is used per mole of Compound 1. At the end of the reaction, the product is not isolated, and is used in-situ for the next step.

The structure of Compound 4 is novel. Compound 4 is prepared by reacting Compound 3 (obtained in-situ above) with a base (e.g., potassium tert-butoxide, potassium pentoxide, potassium tert-amylate, sodium ethoxide, sodium tert-butoxide, or the like) in an alcoholic solvent (e.g., anhydrous EtOH). A catalytic amount of base is preferably used, generally, about 5-20 mol % per mol of Compound 3 in the alcoholic solvent. More preferably, about 15 mol % of base is used. Preferably, the reaction mixture is heated to about 75-85° C. for about 1 hour. At the end of reaction, the product is not isolated, and is used in-situ for the next step.

The structure of Compound Salt 5K is novel. Compound 4 can be converted to Compound Salt 5K by reacting it in-situ with from about 1 to about 3 moles (e.g., 1.5 moles) of a N—$R^2$-substituted carbamate, $R^2NHCO_2R^1$ (e.g., the urethane $EtNHCO_2Et$), and from about 1 to about 3 moles (e.g., 2.1 moles) of a base (e.g., potassium tert-butoxide, potassium pentoxide, potassium tert-amylate, sodium ethoxide, sodium tert-butoxide, or the like), in an ethereal organic solvent (e.g., THF, diethyl ether, monoethyl ether, monoglyme, diglyme, ethylene glycol, or the like) or a sulfolane, at 80-130° C. (preferably 115-125° C.), wherein $R^1$ and $R^2$ are each independently defined as above. The base provides a metal ion (M+) to Compound Salt 5K. Potassium tert-butoxide provides a potassium ion (K+), while sodium tert-butoxide provides a sodium ion (Na+) to Compound Salt 5K. The inventive methodology provides an efficient synthesis for directly converting (in one step) Compound 4 to Compound Salt 5K in solution without the use of any toxic chemicals or harsh thermal conditions.

The potassium Compound Salt 5K is isolated by filtration, but not dried. Compound Salt 5K is selectively N-3 alkylated in-situ to Compound 6 with $BrCH_2$-L (e.g., 2-bromoethyl acetate in an anhydrous, organic solvent (e.g., THF, methyl tert-butyl ether, or the like) in the presence of a phase transfer catalyst (e.g., tetrabutylammonium bromide, tetrabutylammonium hydrogen sulfate, or the like), wherein L is defined as above. The reaction takes place rapidly (e.g., about 1 hour at about 65-70° C.), and no base is required. This is in contrast to known N-alkylation reactions, many of which use dimethylformamide ("DMF") and potassium carbonate or an organic base (e.g., triethylamine, diisopropylethylamine, etc.) to achieve the N-alkylation, and which generally take from several hours to days to complete.

Alternatively, the potassium Compound Salt 5K can be neutralized with an acid (e.g., aqueous acetic acid, dilute hydrochloric acid, dilute sulfuric acid, or the like) to provide Compound 5. Under this alternative process, Compound 5 can be selectively N-3 alkylated by treatment with an inorganic base (e.g., potassium carbonate, sodium carbonate, sodium bicarbonate, potassium butoxide, or the like) in a polar solvent (e.g., acetonitrile and its higher homologs, DMF, N,N-dimethylacetamide ("DMA"), 1-methyl-2-pyrrolidinone ("NMP"), or the like) in the presence of a phase transfer catalyst (e.g., tetrabutylammonium bromide, tetrabutylammonium hydrogen sulfate, or the like) and an alkylating agent (e.g., $BrCH_2$-L, where L is defined as above) to provide Compound 6.

The structure of Compound 6 is novel. The conversion from Compound 1 to Compound 6 is a 5-step process that can be carried out in one pot or container. The overall yield for Compound 6 is generally about 45-55%.

The structure of Compound 7 is novel. Compound 6 is regioselectively dihalogenated (e.g., dibrominated or dichlorinated) to Compound 7 under mild conditions with about 2-3 moles (preferably, about 2.7-2.8 moles) of a dihalogenating agent (e.g., a dibrominating agent, such as N-bromo succinimide ("NBS"), dibromo-1,3-dimethyl hydantoin or N-bromo acetamide). The use of a strong acid (e.g., triflic or sulfuric acid) as a catalyst in an amount of about 1-10 mol %, preferably, about 3 mol %, allows the reaction to proceed at room temperature. Alternatively, tetrabutylammonium hydrogensulfate can be used as the catalyst, but it would require an application of heat (e.g., about 80° C.) to drive the reaction to completion. It is preferred that the reaction is run in a dry polar solvent, such as acetonitrile, DMF, NMP, DMA, or a mixture thereof. Under these conditions, the amounts of mono- and tri-bromo side products are minimized.

Compound 7 is coupled with Compound 8 (an $R^4NH_2$ amine) to form Compound 13 via Compound 9, a novel intermediate. Typical coupling reaction conditions for this step generally require the use of a polar, aprotic solvent (e.g., NMP, DMA, or the like), an inorganic base (e.g., potassium carbonate, sodium carbonate, sodium bicarbonate, or the like), and an excess of Compound 8, preferably, up to about 3 moles of Compound 8 per mole of Compound 7. A preferred mild, inorganic base is sodium bicarbonate. The application of heat will drive the reaction to completion faster. For example, at about 130-140° C., the reaction time can be shortened in half, from about 24 hours to about 12 hours.

L is $R^3$ or a protected form of $R^3$ (i.e., where a moiety is attached to $R^3$ for protecting it from reacting with other ingredients). When L is the same as $R^3$, Compound 9 is the same as Compound 13, so the addition of an inorganic base to the intermediate Compound 9 (step (k) (ii) of the summary of the invention) is not necessary. On the other hand, when L is a protected form of $R^3$, deprotection can be accomplished in the same pot, without isolating Compound 9, by using a catalytic amount of an inorganic base (e.g., potassium carbonate, tetrabutylammonium hydroxide, or the like). Protected forms of $R^3$ include $R^3$ moieties substituted with protective groups such as acetate, propionate, pivaloyl, —OC(O)$R^5$, —NC(O)$R^5$ or —SC(O)$R^5$ groups, wherein $R^5$ is H or $C_{1-12}$ alkyl. When the protecting substituent is an acetate group, deprotection is preferably carried out with tetrabutylammonium hydroxide because it results in a faster and cleaner reaction, and product isolation is facile. In another embodiment of the invention, a pivaloyl protecting group can be used in place of the acetate protecting group, and the application of similar chemistry will lead from Compound 5K (or Compound 5) to Compound 13. The deprotection and work-up conditions are adjusted so as to minimize formation of isomeric impurities. For instance, care should be taken to monitor the basicity of the reaction during deprotection because when the deprotection steps are carried out under very strong basic conditions, diastereomers may form.

Specific Synthesis

The general synthesis of Scheme I can be applied to prepare specific xanthines. For example, if $R^1$ is —$OCH_3$, $R^2$ is —$CH_2CH_3$, L is —$CH_2CO_2CH_3$, $R^3$ is —$CH_2OH$, and $R^4$ is

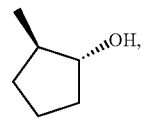

, then the product obtained from Scheme I (Compound 13) can be called 1-ethyl-3,7-dihydro-8-[(1R,2R)-(hydroxycyclopentyl)amino]-3-(2-hydroxyethyl)-7-[(3-bromo-4-methoxyphenyl)methyl]-1H-purine-2,6-dione (Compound 13A), a PDE V inhibitor useful for the treatment of erectile dysfunction. An illustration of this synthesis is shown in the following Scheme II, which allows for an efficient, commercial scale preparation of Compound 13A, without the need for chromatographic purification of intermediates:

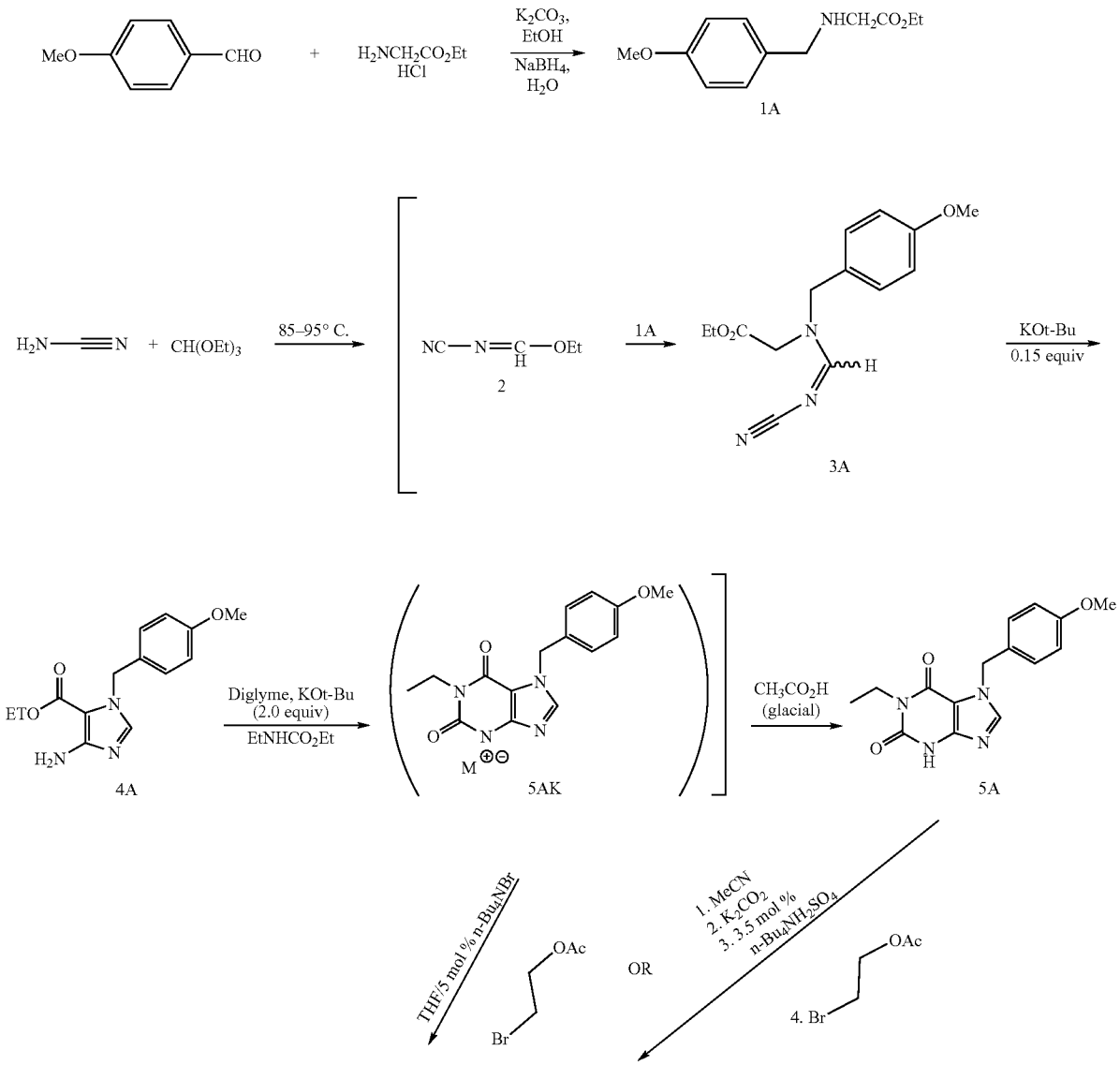

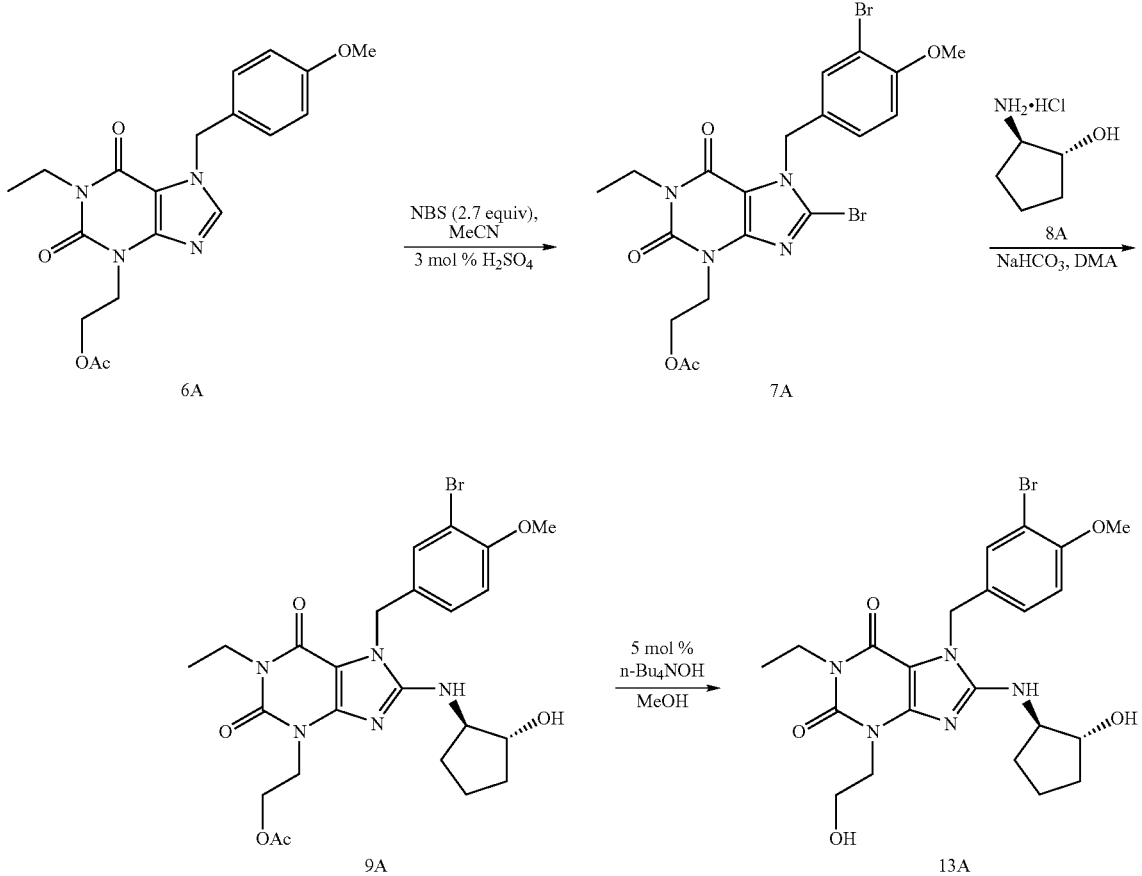

The experimental conditions disclosed herein are preferred conditions, and one of ordinary skill in the art can modify them as necessary to achieve the same products.

EXAMPLES

Compound 1A: glycine-N-[(4-methoxyphenyl)methyl]ethyl ester

To a mixture of glycine ethyl ester hydrochloride (about 1.4 equiv) and potassium carbonate (about 1.0 equiv) was added anhydrous ethanol. The mixture was stirred at about 40-45° C. for about 3 hours. Then, p-anisaldehyde (about 1.0 equiv.) was added, and the reaction mixture was stirred for a minimum of about 3 hours to provide an imine (not shown). Upon reaction completion (about ≦5.0% p-anisaldehyde remaining by GC analysis), the reaction mixture was cooled to about 0-10° C. Then, an aqueous solution of sodium borohydride (about 0.50 equiv) was added to the reaction mixture at a temperature of between about 0° C. and about 20° C., and stirred for about 1 hour to provide Compound 1A. Upon completion of the reduction reaction, the reaction mixture was quenched with the slow addition of an aqueous solution of aqueous glacial acetic acid. After quenching, the reaction mixture was warmed to room temperature and filtered to remove solids. The filtrate was then concentrated under vacuum, followed by the addition of toluene and water to facilitate layer separation. Aqueous potassium carbonate solution was added to adjust the pH of the mixture to about 8-9. The organic layer was separated and the aqueous layer was extracted with toluene. The combined toluene extracts were concentrated to provide the product in about a 80-85% yield (based on GC and HPLC in solution assay).

$^1$H NMR 400 MHz (CDCl$_3$): δ 7.23 (d, J=8.5 Hz, 2H), 6.85 (d, J=8.5 Hz, 2H), 4.17 (q, J=7.1 Hz, 2H), 3.78 (s, 3H), 3.73 (s, 2H), 3.38 (s, 2H), 1.88 (s, br, 1H), 1.26 (t, J=7.1 Hz, 3H); $^{13}$C NMR 100 MHz (CDCl$_3$): δ 172.8, 159.2, 132.0, 129.9, 114.2, 61.1, 55.6, 53.1, 50.4, 14.6.

Compound 2: N-cyanomethanimidic acid ethyl ester

To cyanamide (about 1.2 mole) was added triethylorthoformate (about 1.33 mole), and the reaction mixture was heated to about 85-95° C. for approximately 2 hours to form Compound 2. Estimated in-solution yield was about 95-100%. The product was optionally purified by vacuum distillation.

$^1$H NMR 400 MHz (CDCl$_3$): δ 8.38 (s, 1H), 4.28 (t, J=6.7 Hz, 2H), 1.29 (t, J=6.8 Hz, 3H); $^{13}$C NMR 100 MHz (CDCl$_3$): δ 171.5, 113.4, 65.5, 13.1.

Compound 3A: cis- and trans-glycine N-[(cyanoimino)methyl]-N-[(4-methoxyphenyl)methyl] ethyl ester A solution of Compound 1A (about 1.0 mole) in toluene was concentrated under vacuum to distill off toluene. Anhydrous tetrahydrofuran ("THF") was added to the concentrate, then Compound 2 (about 1.2 moles, obtained above) was added to that, and the solution was heated at reflux for about 1 hour. At this stage, the formation of Compound 3A was complete. Estimated in-solution yield was about 95% (about 2:1 mixture of cis and trans isomers).

Compound 4A: 1H-imidazole-5-carboxylic acid, 4-amino-1-[(4-methoxyphenyl)methyl]ethyl ester Compound 3A (obtained above) was concentrated by distilling off THF. Then, anhydrous ethanol was added to afford a reaction mixture solution. Separately, potassium t-butoxide (about 0.15 mole) was dissolved in anhydrous ethanol to afford a solution. The potassium t-butoxide solution was added to the reaction mixture solution and heated to about 75-85° C. for about 1 hour. The overall in-solution yield of Compound 4A was about 85-90%.

$^1$H NMR 400 MHz (CDCl$_3$): δ 7.16 (s, 1H), 7.08 (d, J=8.6 Hz, 2H), 6.82 (d, J=8.7 Hz, 2H), 5.23 (s, 2H), 4.93 (s, br, 2H), 4.23 (q, J=7.1, 2H), 3.76 (s, 3H), 1.26 (t, J=7.1 Hz, 3H); $^{13}$C NMR 400 MHz (CDCl$_3$): δ 160.9, 159.2, 139.0, 128.6, 128.5, 114.0, 101.8, 59.5, 55.2, 50.1, 14.4.

Compound 5AK: 1-ethyl-3,7-dihydro-7-[(4-methoxyphenyl)methyl]-1H-Purine-2,6-dione potassium salt The reaction mixture containing Compound 4A in ethanol (obtained above) was added to diglyme and distilled under vacuum to remove the ethanol. After being cooled to room temperature, N-ethylurethane (about 1.2 equiv.) was added and the reaction mixture was heated to about 110-120° C. A solution of potassium t-butoxide (2.2 equiv.) in diglyme was added to the hot solution. The reaction mixture was cooled to room temperature. THF was added to precipitate additional product, which was filtered and washed to provide Compound Salt 5AK in 55-65% overall yield. The wet cake can be used as such for conversion to Compound 6A.

$^1$H NMR (DMSO-d$_6$, 400 MHz): δ 7.73 (s, 1H) 7.31 (d, J=8.6 Hz, 2H) 6.86 (d, J=8.6 Hz, 2H) 5.24 (s, 1H) 3.88 (q, J=6.8 Hz, 2H) 3.71 (s, 3H) 1.07 (t, J=6.8 Hz, 3H); $^{13}$C NMR (DMSO-d$_6$, 100 MHz): δ 161.1, 159.0, 158.4, 157.2, 141.4, 131.0, 129.5, 114.1, 105.6, 55.4, 48.2, 34.4, 14.3.

Optional Neutralization of Compound Salt 5AK to Compound 5A:

Compound 5A: 1-ethyl-3,7-dihydro-7-[(4-methoxyphenyl)methyl]-1H-Purine-2,6-dione The wet cake filtered solid of Compound Salt 5AK (obtained above) was suspended in water and then acidified to a pH of about 5 using glacial acetic acid. The resulting slurry was filtered to obtain the neutralized product, which was then washed with water and dried. The overall isolated yield of neutralized Compound 5A from Compound 1A was about 45-55%. Spectroscopic data for neutralized Compound 5A was identical to that of Compound Salt 5AK.

Compound 6A: 3-[2-(acetyloxy)ethyl]-1-ethyl-3,7-dihydro-7-[(4-methoxyphenyl)methyl]-1H-purine-2,6-dione To the wet cake filtered solid of Compound Salt 5AK (obtained above) were added tetrabutylammonium bromide (about 0.05 mole) and 2-bromoethyl acetate (about 1.2 moles) in THF. After being heated to reflux for about 2 hours, part of the THF was distilled off, and isopropyl alcohol was added to the reaction mixture. The reaction mixture was then concentrated under reduced pressure and cooled to around room temperature. Water was added to precipitate the product. After being cooled to about 0-5° C. for about a few hours, the product was isolated by filtration. The wet cake was washed with aqueous isopropyl alcohol (about 30% in water), and dried under vacuum to afford Compound 6A as a pale yellow solid in about a 45-55% overall yield (based on Compound 1A). The crude product may be purified further by decolorizing with Darco in methanol, followed by filtration and concentration to afford crystalline Compound 6A.

$^1$H NMR (CDCl$_3$, 400 MHz): δ 7.54 (s, 1H) 7.32 (d, J=8.6 Hz, 2H) 6.90 (d, J=8.6 Hz, 2H) 5.43 (s, 2H) 4.41 (m, 2H) 4.38 (m, 2H) 4.10 (q, J=7.2 Hz, 2H) 3.79 (s, 3H) 1.96 (s, 3H) 1.25 (t, J=7.2 Hz, 3H); $^{13}$C NMR (CDCl$_3$, 100 MHz): δ 171.1, 160.2, 155.3, 151.4, 148.9, 140.9, 130.1, 127.7, 114.8, 107.5, 61.7, 55.6, 50.2, 42.4, 36.9, 21.2, 13.6.

After Optional Neutralization of Compound Salt 5AK to Compound 5A:

Compound 6A: 3-[2-(acetyloxy)ethyl]-1-ethyl-3,7-dihydro-7-[(4-methoxyphenyl)methyl]-1H-purine-2,6-dione Acetonitrile was added to a mixture of Compound 5A (about 1.0 mole), anhydrous potassium carbonate (about 1.5 moles) and tetrabutylammonium hydrogen sulfate (about 0.05 mole). 2-bromoethyl acetate (about 1.5 moles) was added in three separate portions (0.72 mole in the beginning, another 0.45 mole after about 2 hours of reaction, and then the remaining 0.33 mole after about another 1 hour of reaction) during the course of the reaction at about 80-85° C. The total reaction time was about 7 hours. The reaction mixture was cooled to about room temperature and filtered. The filtrate was concentrated. Aqueous isopropanol was added to crystallize the product. The product was filtered, washed with aqueous isopropanol, and dried to provide Compound 6A in about a 75-80% yield.

Compound 7A: 8-bromo-1-ethyl-3-[2-(acetyloxy)ethyl]-3,7-dihydro-7-[(3-bromo-4-methoxyphenyl)methyl]-1H-Purine-2,6-dione Compound 6A (about 1 mole) and NBS (about 2.8 moles) were dissolved in dry acetonitrile and agitated at about 15-20° C. To this reaction mixture, a solution of sulfuric acid (about 0.03 mol) in acetonitrile was added, while maintaining the reaction temperature below about 25° C. The reaction mixture was agitated at about 20-25° C. for about 12-15 hours until complete consumption of the starting material was indicated. The reaction mixture was cooled to about 0-5° C. and a cold (about 5-10° C.) aqueous solution of sodium sulfite was added, keeping the temperature below about 10° C. The reaction was agitated for about 2 hours at about 0-10° C., and then filtered. The isolated cake was washed with water, followed by methanol, then dried under a vacuum to obtain Compound 7A in about an 85% yield.

$^1$H NMR (CDCl$_3$, 400 MHz): ☐ 7.60 (d, J=2.0 Hz, 1H), 7.35 (dd, J=8.4 Hz, 2.0 Hz, 1H), 6.83 (d, J=8.4 Hz, 1H), 5.43 (s, 2H), 4.35 (m, 4H), 4.05 (q, J=7.0 Hz, 2H), 3.85 (s, 3H), 1.96 (s, 3H), 1.23 (t, J=7.0 Hz, 3H); $^{13}$C NMR (CDCl$_3$, 100 MHz): ☐ 171.0, 156.2, 154.2, 150.8, 148.2, 138.3, 128.9, 128.7, 127.5, 112.1, 112.0, 109.1, 61.5, 56.5, 49.3, 42.5, 37.0, 21.0, 13.3. MS (ES) m/e 545.2 (M+H)$^+$.

Compound 13A: 1-ethyl-3,7-dihydro-8-[(1R,2R)-(hydroxycyclopentyl)amino]-3-(2-hydroxyethyl)-7-[(3-bromo-4-methoxyphenyl)methyl]-1H-Purine-2,6-dione Compound 7A (about 1 mole) was combined with (R,R)-2-amino-1-cyclopentanol hydrochloride (Compound 8A, about 1.2 moles) and sodium bicarbonate (about 3 moles). To this reaction mixture was added N,N-dimethylacetamide ("DMA"), and the reaction mixture was agitated at about 135-140° C. for about 15-17 hours until complete consumption of the starting material was indicated. Compound 9A is an intermediate that is formed, but not isolated, from the reaction mixture. The reaction mixture was then cooled to about 45-50° C., and tetrabutylammonium hydroxide (about 0.05 moles of about a 40% solution in water) was charged therein, followed by methanol. The reaction mixture was refluxed at about 80-85° C. for about 8-9 hours until complete deprotection of the acetate group was indicated. The reaction mixture was cooled to about 40-45° C. and concentrated under vacuum. The pH of the reaction mixture was adjusted to about 5-6 with dilute acetic acid, and the reaction mixture was heated to about 55-65° C., and seeded with a small amount of Compound 13A. The reaction mixture was then cooled to about 30-35° C. over a period of about 2 hours, and water was added over a period of about 1 hour. The reaction mixture was further cooled to about 0-5° C. over a period of about 1 hour, and agitated at that temperature for about 4 hours. The Compound 13A product was isolated by filtration, washed with water and dried to provide about an 85-90% yield.

$^1$H NMR (CDCl$_3$, 400 MHz): □ 7.47 (d, J=2.1 Hz, 1H), 7.18 (dd, J=8.4 Hz, 2.0 Hz, 1H), 6.87 (d, J=8.4 Hz, 1H), 5.23 (s, 2H), 5.01 (s, 1H), 4.22 (m, 2H), 4.15 (m, 1H), 4.05 (q, J=7.0 Hz, 2H), 3.93 (m, 3H), 3.88 (s, 3H), 3.77 (m, 1 H), 2.95 (m, 1H), 2.15 (m, 1H), 2.05 (m, 1H), 1.60-1.80 (m, 4H), 1.35 (m, 1H), 1.23 (t, J=7.0 Hz, 3H); $^{13}$C NMR (CDCl$_3$, 100 MHz): □ 156.2, 154.0, 153.5, 151.8, 148.3, 132.6, 129.1, 127.9, 112.5, 103.2, 79.5, 77.8, 63.2, 61.3, 56.7, 46.5, 45.9, 36.8, 32.9, 31.5, 21.4, 13.8. MS (ES) m/e 523.4 (M+H)$^+$.

Micronization

Materials prepared by the above-described processes without further processing can exhibit particle sizes that are greater than optimal for purposes of bioabsorption, and thus, bioavailability. In certain preferred embodiments of the invention, the compounds disclosed herein are subject to a micronization process to generate particle size distributions more favorable for bioabsorption.

Form 2 of Compound 13 (disclosed in the co-pending patent application "Xanthine Phosphodiesterase V Inhibitor Polymorphs," incorporated by reference thereto) was micronized on a fluid energy mill (Jet Pulverizer Micron Master, model 08-620). A feeder (K-Tron Twin Screw Feeder) was used to feed material to the mill at a rate of about 80 grams/min. A mill jet pressure of 110 psig was used. The resulting material was then heated to convert amorphous material generated during micronization to crystalline material. The setpoint on the dryer (Stokes Tray Dryer, model 438H) was set to 95° C. The batch was heated at a temperature between 90 and 100° C. for 8 hours. Differential Scanning Calorimetry ("DSC") analysis indicated no amorphous material was present. The particle size distribution of the resulting material was characterized, using a Sympatec particle size analyzer, as having a volume mean diameter of 8.51 μm and a median particle diameter of 5.92 μm. Cryogenic micronization processes may result in even more favorable particle size distributions.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A method for producing a compound of formula 13A:

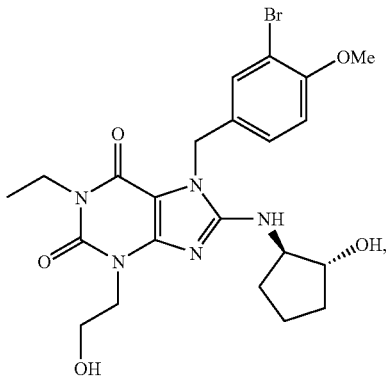

the method comprising:
(i) reacting a compound of formula 7 with a primary amine Compound of Formula 8 or a hydrochloride salt thereof, in the presence of a base to form a compound of formula 9:

wherein L is a protecting group which is acetate, propionate, a pivaloyl protecting group, —OC(O)R$^5$, or —NC(O)R$^5$, wherein R$^5$ is H or C$_{1-12}$ alkyl and, wherein R$^4$ is alkyl, cycloalkyl, cycloalkenyl, heterocycloalkyl, aryl or heteroaryl, and R$^4$ is optionally substituted with one or more halo, nitro amino, or —C(O)OR$^{50}$ substituents, wherein —R$^{50}$ is H, Alkyl, cycloalkyl, heterocycloalkyl, heteroaryl or aryl; and
(ii) treating the compound of formula 9 with a base to remove the protecting group thereby forming a compound of Formula 13A wherein Compound 7 is Compound 7A, Compound 8 is Compound 8A, Compound 9 is Compound 9A and the base in step (i) is sodium bicarbonate, and wherein the reaction is carried out in the presence of N,N-dimethyl acetamide as a solvent: according to the following scheme

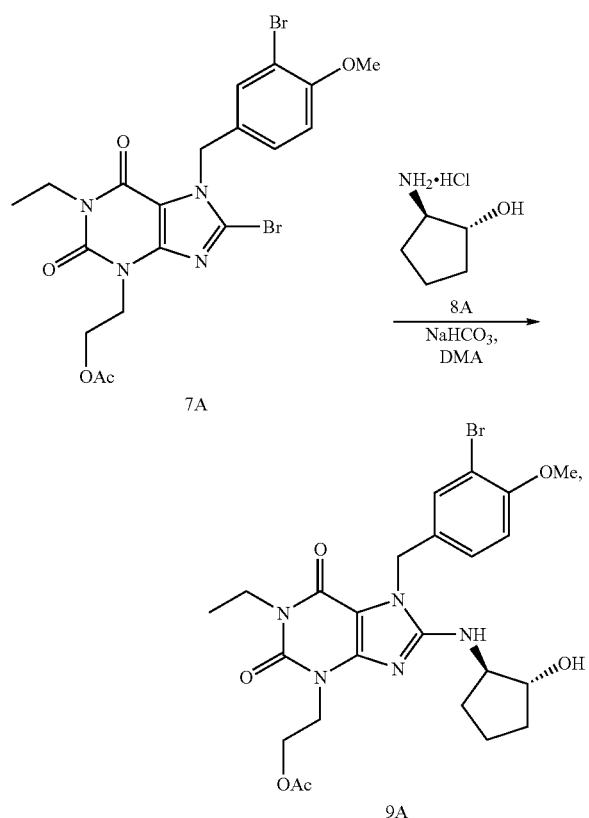

wherein,
DMA is N,N-dimethyl acetamide
Me is CH$_3$—; and
OAc is acetate.

2. The method of claim 1 wherein said compound of formula 7A is prepared by dihalogenating a compound of formula 6A in accordance with the reaction scheme:

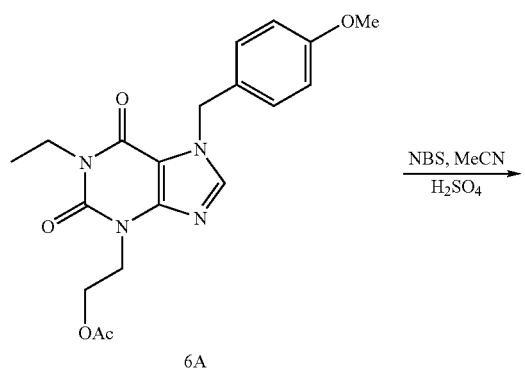

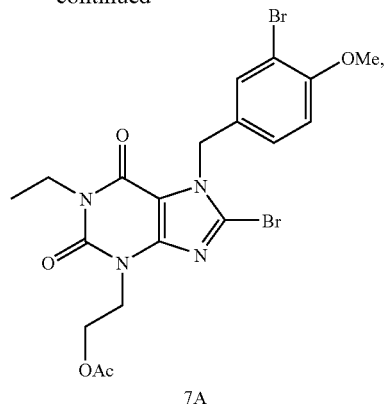

wherein said reaction scheme comprises dibrominating Compound 6A using N-bromosuccinimide in acetonitrile as a solvent and sulfuric acid as a catalyst and wherein:
MeCN is acetonitrile:
NBS is N-bromosuccinimide,
Me is CH$_3$—; and
QAc is acetate.

3. The method of claim 1 wherein the base in step (ii) is tetrabutylammonium hydroxide, the addition of which is followed by the addition of methanol:

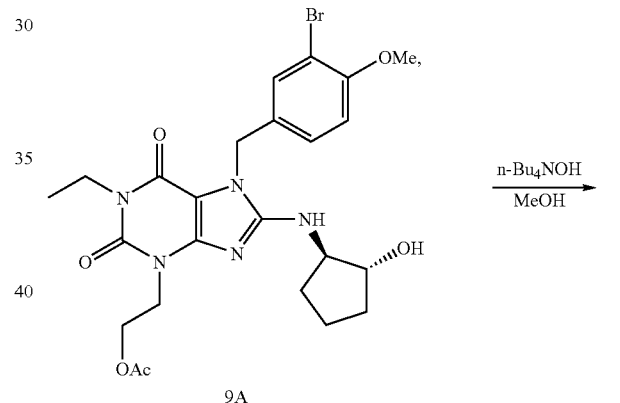

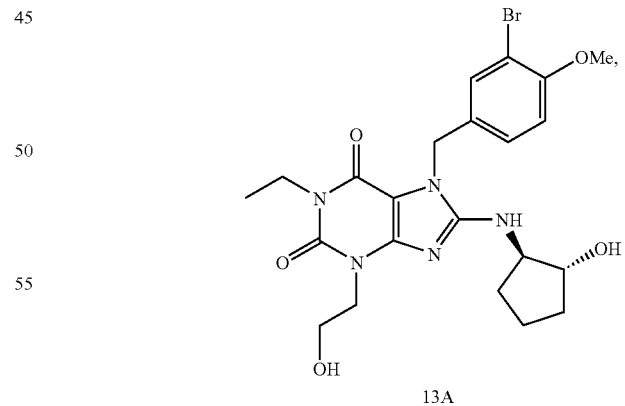

wherein,
n-BU4NOH is tetrabutylammonium hydroxide;
Me is CH$_3$—; and
OAc is acetate.

* * * * *